US012776412B2

(12) United States Patent
Keynan

(10) Patent No.: US 12,776,412 B2
(45) Date of Patent: Oct. 27, 2026

(54) FLOW BASED DYNAMIC CONNECTIVITY SYSTEM

(71) Applicant: Given Imaging LTD., Yoqneam (IL)

(72) Inventor: Roni Keynan, Hadera (IL)

(73) Assignee: Given Imaging LTD., Yoqneam (IL)

( * ) Notice: Subject to any disclaimer, the term of this patent is extended or adjusted under 35 U.S.C. 154(b) by 698 days.

(21) Appl. No.: 17/916,828

(22) PCT Filed: May 13, 2021

(86) PCT No.: PCT/IL2021/050560
§ 371 (c)(1),
(2) Date: Oct. 4, 2022

(87) PCT Pub. No.: WO2021/234690
PCT Pub. Date: Nov. 25, 2021

(65) Prior Publication Data
US 2023/0162852 A1 May 25, 2023

Related U.S. Application Data

(60) Provisional application No. 63/026,139, filed on May 17, 2020.

(51) Int. Cl.
*G16H 40/63* (2018.01)
*H04W 76/25* (2018.01)

(52) U.S. Cl.
CPC ............ *G16H 40/63* (2018.01); *H04W 76/25* (2018.02)

(58) Field of Classification Search
CPC ........ G16H 40/63; G16H 40/40; G16H 40/67; H04W 76/25; A61B 1/041; A61B 1/00016
See application file for complete search history.

(56) References Cited

U.S. PATENT DOCUMENTS

2004/0179512 A1* 9/2004 Leblanc .................. H04L 67/04 370/328
2006/0104235 A1* 5/2006 Fritz ..................... H04W 88/02 370/328

(Continued)

FOREIGN PATENT DOCUMENTS

CN 102178536 A 9/2011
CN 104754641 A 7/2015

(Continued)

OTHER PUBLICATIONS

Unknown, "TCP keepalive overview", Jun. 7, 2007 (Jun. 7, 2007), p. 1-3, Retrieved from the Internet: URL:https://tldp.org/HOWTO/TCP-Keepalive-HOWTO/overview.html XP055834157 [retrieved on Aug. 23, 2021].

(Continued)

*Primary Examiner* — Charles T Shedrick
(74) *Attorney, Agent, or Firm* — Carter, DeLuca & Farrell, LLP

(57) ABSTRACT

A Dynamic Connectivity System (DCS) comprising a patient module configured for communication with an in-vivo device and with at least one additional device; the DCS further comprises a gateway device configured for providing an access point for the patient module for accessing a network; the access point is configured for termination after an idle period of predetermined idle time, and the patient module is configured for uploading data to the network via the mobile device during a non-idle period of the gateway device; the patient module is also configured for sending, during the idle period, a pinging signal to the mobile device different from the data, the pinging signal having a period time shorter than the predetermined idle time, thereby interrupting the idle period and preventing termination of the access point.

17 Claims, 3 Drawing Sheets

(56) References Cited

U.S. PATENT DOCUMENTS

| | | | | |
|---|---|---|---|---|
| 2011/0222465 | A1* | 9/2011 | Arashin | H04W 76/14 370/315 |
| 2013/0235795 | A1* | 9/2013 | Huang | H04L 1/16 370/328 |
| 2015/0070503 | A1* | 3/2015 | Kraeling | H04N 23/66 348/148 |
| 2015/0078522 | A1* | 3/2015 | Makino | A61B 6/4405 378/96 |
| 2015/0158513 | A1* | 6/2015 | Costa | B61L 23/04 348/144 |
| 2016/0000300 | A1* | 1/2016 | Williams | A61B 1/05 600/109 |
| 2016/0317070 | A1* | 11/2016 | Sivaraman | A61B 5/7282 |
| 2016/0330675 | A1 | 11/2016 | Reitsma et al. | |
| 2017/0180972 | A1 | 6/2017 | Kim et al. | |
| 2018/0353073 | A1* | 12/2018 | Boucher | A61B 5/05 |
| 2019/0120785 | A1* | 4/2019 | Halac | A61B 5/14532 |
| 2023/0249351 | A1* | 8/2023 | Tan | B25J 9/1682 700/258 |

FOREIGN PATENT DOCUMENTS

| | | | | |
|---|---|---|---|---|
| CN | 110325954 | A1 | 10/2019 | |
| CN | 111050415 | A | 4/2020 | |
| CN | 118890105 | A * | 11/2024 | H04W 24/08 |
| JP | 2011511584 | A | 4/2011 | |
| JP | 2011528198 | A | 10/2011 | |
| JP | 2016063315 | A | 4/2016 | |
| JP | 2020039104 | A | 3/2020 | |
| WO | 2010070906 | A1 | 6/2010 | |

OTHER PUBLICATIONS

Challa, Sravani et al., "Authentication Protocols for Implantable Medical Devices: Taxonomy, Analysis and Future Directions", Dec. 13, 2017 (Dec. 13, 2017), vol. 7, No. 1, p. 57-65, XP011674504.

International Search Report and Written Opinion of the International Searching Authority issued in corresponding application PCT/IL2021/050560 mailed Nov. 3, 2021 (18 pages).

European Examination Report for EP 21 736 749.9 dated Aug. 1, 2024, 6 pages.

Chinese Office Action for Application No. 202180035912.0 dated Jul. 15, 2025 with English translation, 23 pages.

Notice of Allowance dated Jun. 2, 2025 issued in corresponding Japanese Patent Application No. 2022-570141 (4 pages).

Chinese Office Action for Application No. 202180035912.0 dated May 22, 2026 with English translation, 12 pages.

* cited by examiner

FLOW BASED DYNAMIC CONNECTIVITY SYSTEM

CROSS REFERENCE TO RELATED APPLICATIONS

The present application is a U.S. National Stage Application filed under 35 U.S.C. § 371(a) of International Patent Application No. PCT/IL2021/050560, filed May 13, 2021, which claims the benefit of and priority to U.S. Provisional Application No. 63/026,139, filed May 17, 2020, both of which are hereby incorporated by reference herein in their entirety.

TECHNOLOGICAL FIELD

The present invention is in the field of communication, particularly, communication configured for uploading data to the cloud.

BACKGROUND OF THE INVENTION

A hotspot is a physical location where people may obtain Internet access, typically using Wi-Fi technology, via a wireless local-area network (WLAN) using a router connected to an Internet service provider.

Hotspots may be public hotspots, e.g. created by a business for use by customers to provide Internet access, controlled to some degree by the venue. In its simplest form, venues that have broadband Internet access can create public wireless access by configuring an access point (AP), in conjunction with a router to connect the AP to the Internet.

A private hotspot, often called tethering, may be configured on a smartphone or tablet that has a network data plan, to allow Internet access to other devices via Bluetooth pairing, or through the RNDIS protocol over USB, or even when both the hotspot device and the device(s) accessing it are connected to the same Wi-Fi network but one which does not provide Internet access. Similarly, a Bluetooth or USB OTG can be used by a mobile device to provide Internet access via Wi-Fi instead of a mobile network, to a device that itself has neither Wi-Fi nor mobile network capability.

Acknowledgement of the above references herein is not to be inferred as meaning that these are in any way relevant to the patentability of the presently disclosed subject matter.

GENERAL DESCRIPTION

In accordance with one aspect of the subject matter of the present application, there is provided a Dynamic Connectivity System (DCS) comprising:

- a patient module configured for communication with an in-vivo device receiving data therefrom, and for communication with at least one additional device; and
- a gateway device configured for providing an access point for said patient module for accessing a network;

wherein said access point is configured for termination after an idle period of a predetermined idle time, and wherein said patient module is configured for at least the following:

- uploading data to said network via said gateway device while said access point is active; and
- sending, during said idle period, a pinging signal to said gateway device in predetermined time intervals, said intervals having a period time shorter than said predetermined idle time, thereby preventing termination of said access point.

The data uploaded to the network via said gateway device may be at least any one of the following:

- raw data obtained from the in-vivo device;
- processed data obtained from the in-vivo device;
- data processed by the patient module based on raw/processed data obtained from the device; and
- data based on any of the above.

The term 'idle period' should be understood herein in the context of the present application as a period of time in which no such data is transferred to the network via said gateway device.

The DCS may constitute part of a larger system comprising an HCP module, a gateway module comprising the gateway device, a medical kit comprising the patient module, and the cloud.

The DCS may be configured for providing communication between an in-vivo device (e.g. capsule endoscopy, pacemakers etc.) and the network. The patient module may be a wearable device configured for receiving data from said in-vivo device and said gateway device may be a mobile device such as a smartphone, tablet etc. In accordance with a specific example, the in-vivo device may be an endoscopy capsule, and the wearable device may be an adhesive patch (stick-to-skin solution), comprising the required communication components to send/receive data to/from the in-vivo device and for uploading data obtained from the in-vivo device to the cloud via said gateway device.

The gateway device may be configured for granting the patient module with access to the internet either by connecting it to a router which, in turn, provides access to the internet, or directly to the internet via a data plan (i.e. tethering). Under the above configuration, the gateway device constitutes an access point (AP) while the patient module constitutes the client.

Communication between the patient module and the gateway device may be performed using one or more communication channels, e.g. WiFi, Bluetooth, Bluetooth Low Energy (BLE) etc.

The communication between the patient module and the gateway device may facilitate at least the following:

- signaling—providing notifications and instructions to the patient. In case the gateway device is also a display device (e.g. a smartphone), such notifications and instructions may be provided to the patient via an appropriate app;
- data transfer—data obtained from the in-vivo device, and/or processed by the in-vivo device and/or wearable device; and
- control—informing the patient module about additional devices attempting to gain access thereto.

In accordance with a specific example, the WiFi channel may be used for transferring of raw/processed data, while one or more BLE channels may be used for signaling and control. It should be noted that both the WiFi and BLE may operate at similar broadcasting frequencies but may have different bandwidths and occupy different timeslots during communication.

The predetermined idle time of the gateway device may be in the range of 60-100 seconds, more particularly between 75 and 85 seconds, and even more particularly, around 90 second. The pinging signal may have a period in the range of 40 to 80 seconds, more particularly 50 to 70 seconds, and even more particularly, around 60 seconds.

The patient module may be configured for chunking the data into chunks before transferring the data to the gateway device. The patient module may be configured for uploading these data chunks using said gateway device in predetermined time intervals, referred to herein as Data Upload time intervals or DU time intervals, corresponding to the time required for obtaining such chunks of data. The DU time intervals may be greater than said idle period, for example, in the range of 200 to 400 seconds, more particularly 250 to 350 seconds, and even more particularly, around 300 seconds. The data chunks may range between 10 MB and 100 MB, and, in accordance with a particular example, be between 40 MB and 60 MB;

The patient module may be configured to upload to the network, via said gateway device, data that has accumulated thereon during said DU time interval, wherein, within said DU time interval, the patient module may be configured for sending the pinging signal in order to prevent the gateway device from terminating owing to an extensive idle period.

The configuration may be such that during data transfer from the patient module to the network via the gateway device, the pinging signal to the gateway device is disabled. In other words, the pinging signal may be used only during an idle period of said gateway device.

The patient module may also be configured for sending a secondary pinging signal to the gateway device in order to verify that the gateway device is active. This secondary pinging signal may be sent periodically, with a period considerably shorter than said pinging signal, for example, 5, 10 or 15 seconds and may also use the BLE channel.

In accordance with the subject matter of the present application, the DCS may also be configured for accommodating communication with a data device configured for displaying and or further processing raw/processed data and/or information based thereon.

In accordance with one example, the data device may be configured for communicating directly with the patient module. Under this configuration, when a data device requests access to the patient module, the latter may be configured for switching from a client mode to an AP mode, providing access to the data device which, in turn, functions as the client. Hereinafter, this mode of operation will be referred herein as Real Time View (RTV). It should be noted that under this configuration, the patient module may continuously advertise its presence via a second BLE channel different than the first BLE channel in order to be discoverable by the data device.

The patient module may be configured for prioritizing the data device over uploading data to the network via said gateway device. In addition, when the RTV mode is active, uploading of data to the gateway device may be paused. However, the patient module may still be configured for prioritizing maintaining the hotspot alive over the RTV mode, wherein it may periodically switch back to a client mode in order to continue sending the pinging signal, after which it may revert to serving as the AP for the data device.

In accordance with another example, the data device may be configured for communication with the cloud and downloading therefrom the raw/processed data previously uploaded by the patient module. This mode of operation will be referred hereinafter as a Near Real Time View (NRTV).

Under this mode of operation, once a request by the data device is provided to the cloud it may also notify the patient module about said request, wherein the patient module may switch to transferring data to the gateway device continuously, rather than chunking the data, thereby improving the NRTV.

The DCS of the present application provides a seamless and dynamic switching between two operational modes: data upload to the cloud via the gateway device and data transfer to an HCP device. In addition, in each of the operational modes the data is transferred over a different network and under a different configuration, thereby enhancing data safety and creates a buffer between the HCP device and the patient's data uploaded to the cloud.

In accordance with another aspect of the subject matter of the present application there is provided a Dynamic Connectivity System (DCS) comprising a patient module configured for communication with an in-vivo device and for receiving data therefrom, said patient module being configured for communicating in at least the following modes:

- a client mode in which the patient module communicates with a gateway device configured for providing the patient module with an access point for accessing a network; and
- an access point (AP) mode in which the patient module authorized access for a data device configured for receiving data from said patient module;
- and wherein said patient module is configured for dynamically switching between the client mode and the AP mode.

The DCS system may operate in the client mode by default, and configured for switching to the AP mode upon request from the data device. As in the previous aspect of the subject matter of the present application, the patient module is configured for prioritizing the AP mode over the client mode when access is requested by the data device. However, the patient module may prioritize keeping the gateway device's hotspot alive over the AP mode.

All features previously described in connection with the first aspect of the subject matter of the present application, e.g. the use of BLE channels for communication with the gateway device and the data device, advertising the presence of the patient module, sending a pinging signal etc. may be implemented in the current aspect mutatis mutandis.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

Figure 1:
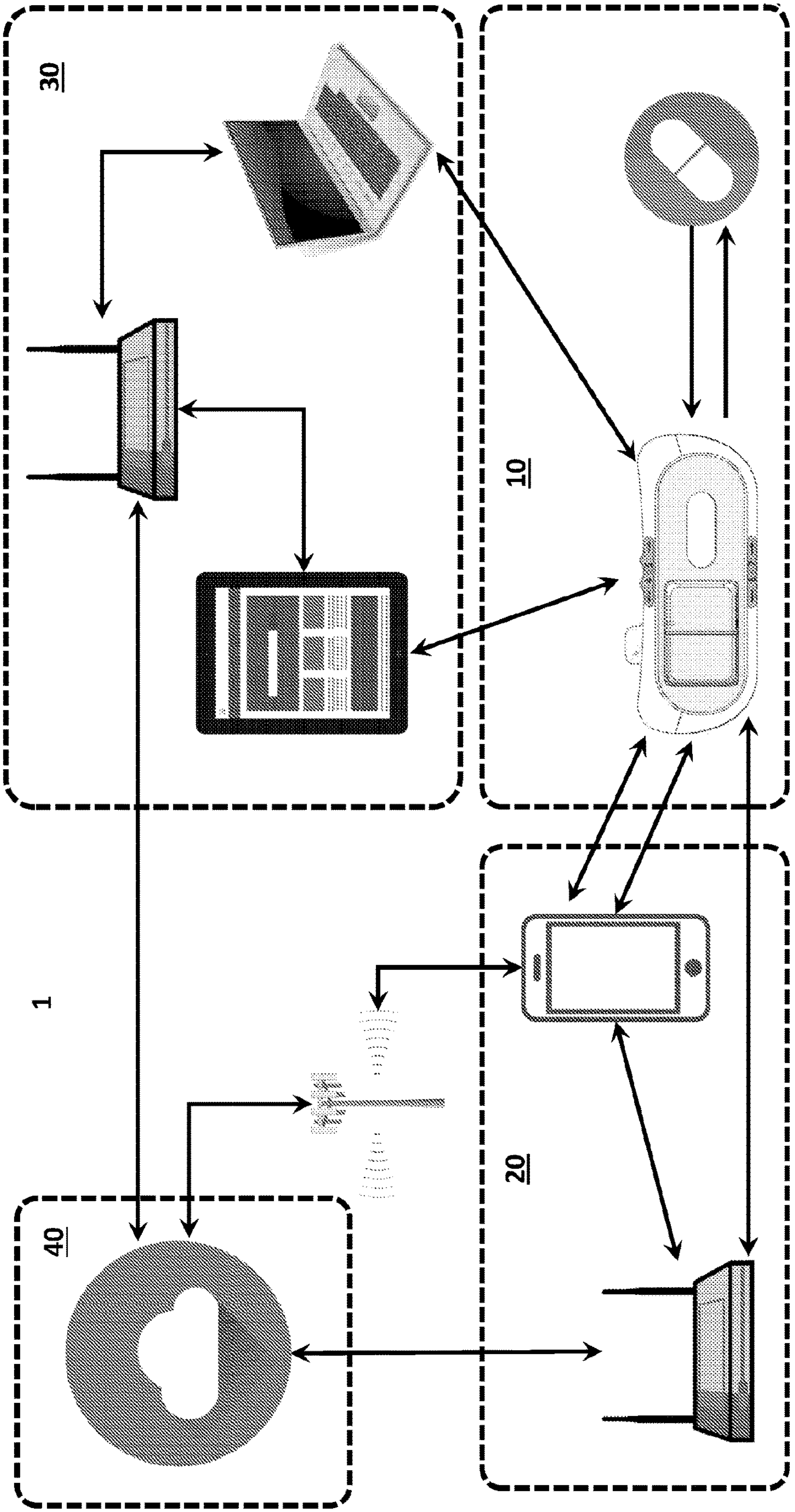
FIG. 1 is a schematic illustration of a comprehensive system, comprising the DCS of the present application.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF EMBODIMENTS

Attention is first drawn to FIG. 1, in which a comprehensive system is shown, generally designated 1 and comprising a medical kit module 10, a gateway module 20, an HCP module 30 and the cloud 40. The Dynamic Connectivity System (DCS) of the present application is established between the medical kit 10 and the gateway module 20, and between the medical kit 10 and the HCP module 30.

In the following example, the comprehensive system is shown as part of a capsule endoscopy procedure, wherein the medical kit 10 comprises a swallowable endoscopy capsule 50 constituting the in-vivo device and an adhesive patch 60 constituting a patient module, configured for communication therebetween using an uplink channel 62 and a downlink channel 64.

Figure 2A:
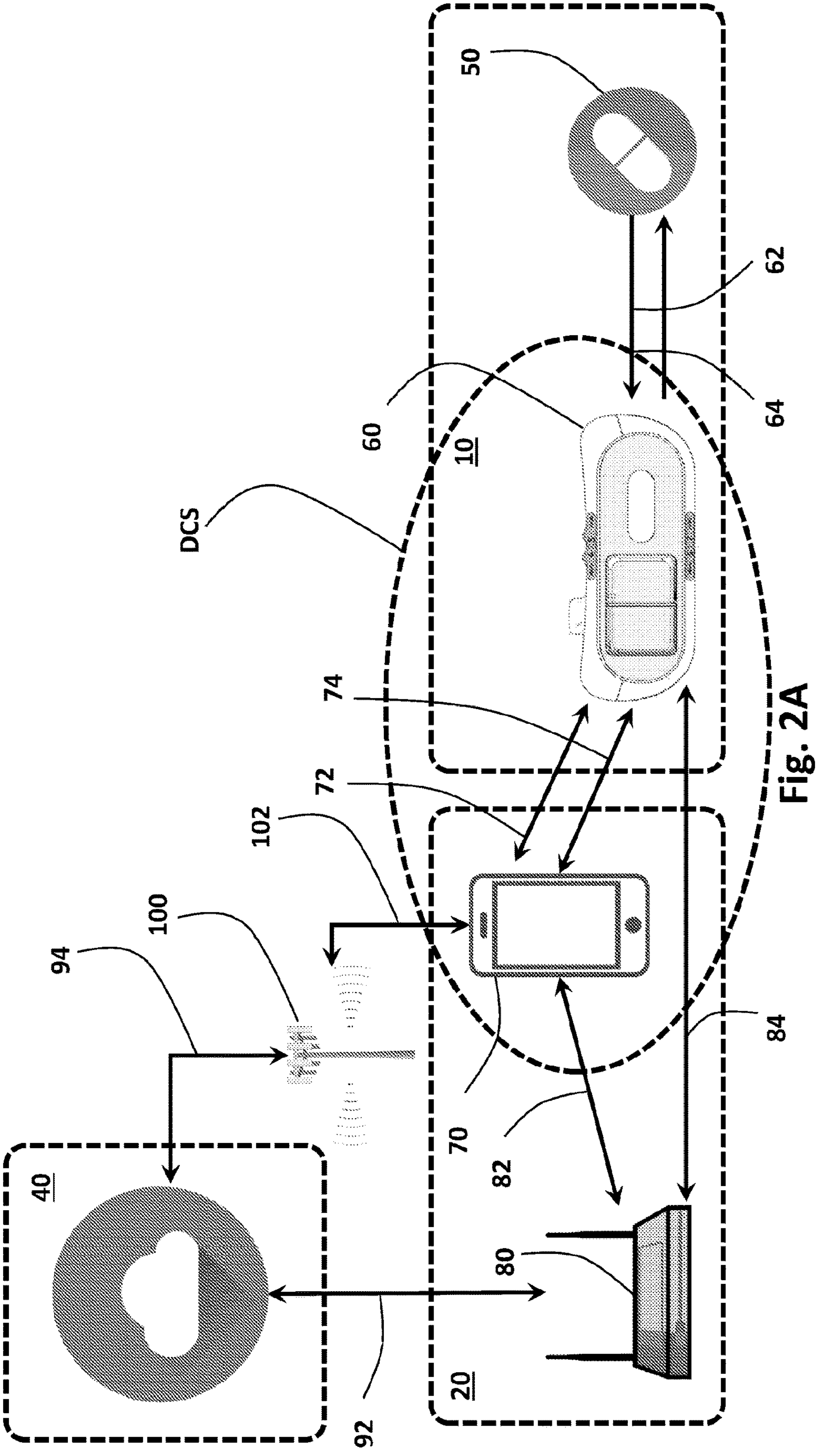
FIG. 2A is a schematic representation of the DCS of the present application when connecting a medical kit, a gateway module and the cloud.

Attention is now drawn to FIG. 2A, in which the DCS is shown providing communication between the medical kit 10 and the gateway module 20. The patch 60 is configured for receiving data from the capsule 50 and for uploading data to the cloud 40. It should be noted that the data uploaded to the cloud may be any of the following:

raw data obtained from the in-vivo device;

processed data obtained from the in-vivo device;

data processed by the patient module based on raw/processed data obtained from the device; and data based on any of the above.

The patch 60 is configured for uploading data to the cloud 40 either by direct communication 84 with the router 80, or via a hotspot established by a mobile device 70. The patch 60 is configured for communicating with the mobile device 70 via secure Wi-Fi 72 and via a first Bluetooth Low Energy (BLE) channel 74. Under this configuration, the mobile device 70 serves as an Access Point (AP) while the patch 60 functions as the client. The WiFi channel 72 is used in order to transfer acquired/processed data to the mobile device 70 while the BLE channel 74 is used for providing the mobile device 70 with notification and instructions related to the CE procedure, as well as a control signal checking that the mobile device 70 is active, in range etc.

It is noted that when the mobile device 70 establishes a hotspot, it connects the patch 60 to the cloud 40 via a cell antenna 100 (indicated by connections 102 and 94), or to the router 80 via connection 82.

When the patch 60 is connected to the cloud 40 via the mobile device 70 and cell antenna 100, the mobile device 70 is configured for terminating the hotspot within ninety seconds if no data is provided thereto by the patch 60. On the other hand, the patch 60 is configured for uploading data to the cloud 40 in chunks of predetermined size, and until such a data chunk is accumulated, the patch 60 will not transmit it to the mobile device 70.

This can create a situation in which the mobile device's hotspot remains idle for over ninety seconds, causing termination of the hotspot. Thereafter, if the patch 60 is required to upload data there will be a need to reestablish the hotspot, causing a delay in communication. In order to overcome this deficiency, the DCS is provided, according to which the patch 60 is configured for periodically sending a pinging signal to the mobile device 70, with a time period shorter than ninety seconds (in this example—sixty seconds). Thus, even if data is not being uploaded to the cloud 40 via the hotspot during the entire idle period, the hotspot will remain active and the hotspot will not be terminated.

In accordance with a particular example, the patch 60 is also configured for sending a secondary pinging signal via the first BLE channel 74 every five to fifteen seconds, configured for verifying that the mobile device 70 is active (hadn't shut down, is in range etc.).

Figure 2B:
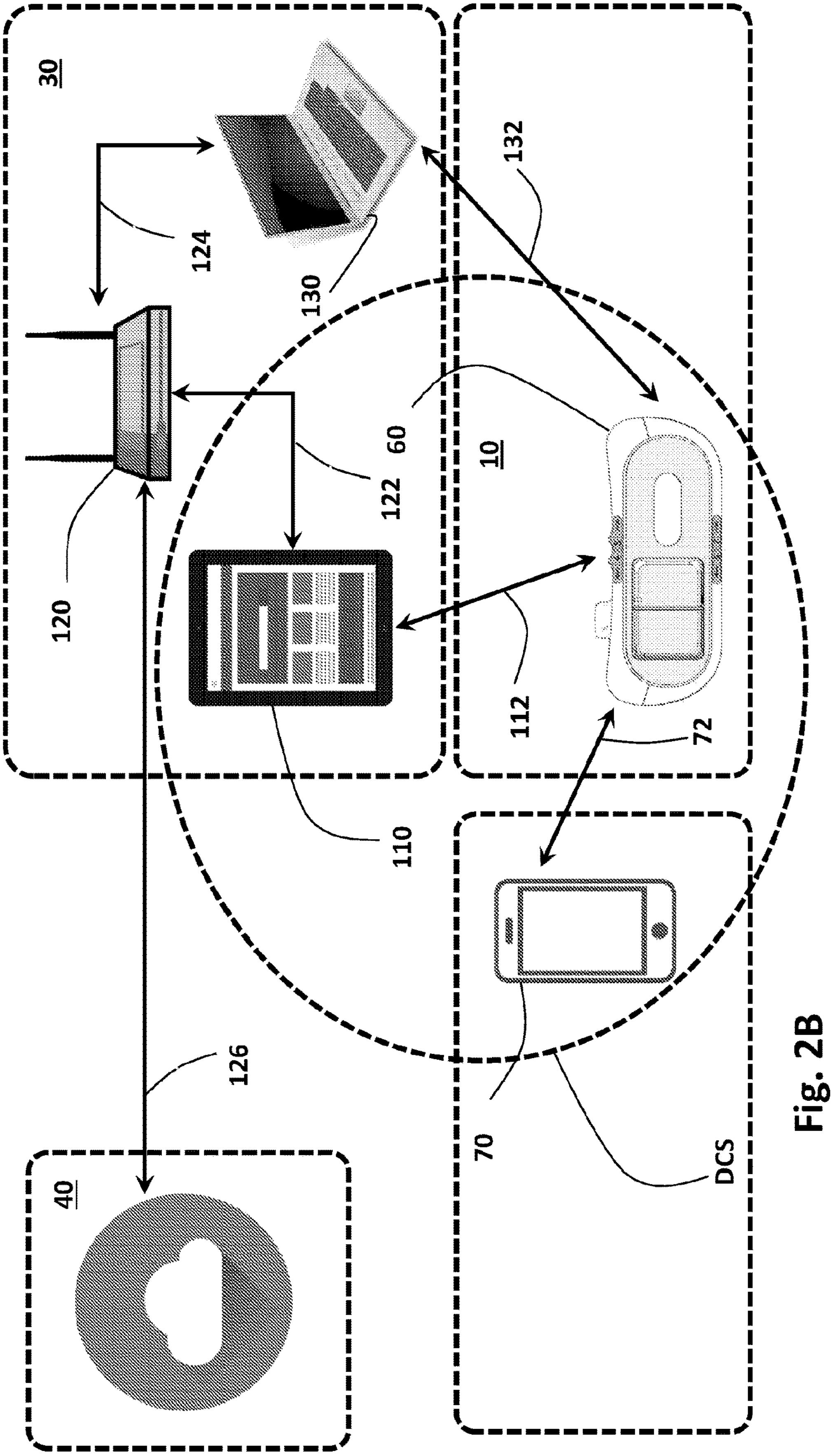
FIG. 2B is a schematic representation of the DCS of the present application when connecting a medical kit, a gateway module and an HCP module.

Turning now to FIG. 2B, the DCS is shown providing communication between the HCP module 30, the gateway module 20 and the medical kit 10. In particular, during a capsule endoscopy procedure, an HCP may desire to review the data uploaded from the capsule 50 to the patch 60. In this case, a display device such as a tablet 110 may be used by the HCP to view the data.

Under this configuration, the patch 60 continuously advertises its presence, via a second BLE channel 112, in order to be discoverable by the HCP device 110. When the HCP desires to view the data, the tablet 110 requests access from the patch 60 via BLE connection 112. The patch 60 then verifies that the tablet 110 is authorized to access (in order to prevent unauthorized parties from viewing a patient's data), and grants access.

When the patch 60 receives such a request, it prioritizes the establishment of such a connection with the tablet 110 and switches to functioning as an AP while the tablet 110 functions as a client. In this case, once the connection 112 is established, the patch 60 halts its connection 72 with the mobile device's hotspot, and the HCP can have a Real Time View (RTV) of the data.

However, the patch 60 still prioritizes maintaining the hotspot active over the RTV, wherein after sixty seconds of RTV, the patch 60 will temporarily terminate the connection 112, switch back to functioning as a client for the mobile device 70 and send the pinging signal to maintain the channel 72 open. Thereafter, the patch 60 can switch back to the connection 112 and continue RTV with the HCP tablet 110.

With further reference to FIG. 2B, the HCP may also operate under a Near Real Time View (NRTV), in which case the router 120 of the HCP module 30 establishes a connection 126 with the cloud, downloading therefrom the data. Under this configuration, the patch 60 will no longer buffer the data in chunks, but rather will continuously upload data to the cloud via hotspot. Also in this case, there is not need for sending the pinging signal since the channel 72 with the mobile device 70 is constantly in use (i.e. no idle time).

Those skilled in the art to which this invention pertains will readily appreciate that numerous changes, variations, and modifications can be made without departing from the scope of the invention, mutatis mutandis.

The invention claimed is:

1. A system comprising:

an in-vivo device; and a patient module comprising a wearable device, the patient module configured to:

receive data from the in-vivo device, operate in a client mode, in which the patient module transfers the data to a gateway module, and upon request from a healthcare professional (HCP) device, dynamically switch from the client mode to an access point (AP) mode, in which the patient module authorizes direct access to the data in the patient module by the HCP device via a direct connection between the patient module and the HCP device, the direct connection having no intermediate device, wherein the gateway module comprises a mobile device and is configured to receive the data from the patient module while the patient module operates in the client mode and to upload the data to a cloud server, and wherein the HCP device is configured to operate as a client to directly connect with the patient module while the patient module operates in the AP mode and to access the data in the patient module via the direct connection between the patient module and the HCP device, wherein the gateway module provides an access point while the patient module operates in the client mode, wherein the access point of the gateway module is configured to terminate after an idle period of a predetermined idle time duration, wherein the patient module is further configured to send, during the idle period, a pinging signal to the gateway module, the pinging signal sent at a time interval shorter than the predetermined idle time duration and operating to prevent the access point of the gateway module from terminating, and wherein in the AP mode, the patient module is further configured to, periodically:

switch from the AP mode to the client mode, send the pinging signal to the gateway module, and revert to operating in the AP mode.

2. A system according to claim 1, wherein the wearable device is an adhesive patch, and wherein the adhesive patch comprises communication components configured to receive the data from the in-vivo device and to transfer the data to the gateway module.

3. A system according to claim 1, wherein the gateway module is further configured to provide the patient module with access to the Internet.

4. A system according to claim 1, wherein communication between the patient module and the gateway module is performed using one or more communication channels.

5. A system according to claim 4, wherein the communication between the patient module and the gateway module is performed using communication channels comprising:

a WiFi channel, and a first Bluetooth Low Energy (BLE) channel.

6. A system according to claim 5, wherein the WiFi channel is used for data transfer and the first BLE channel is used for signaling and control.

7. A system according to claim 5, wherein the patient module advertises its presence for discovery by the HCP device via a second BLE channel different from the first BLE channel.

8. A system according to claim 1, wherein the patient module is configured to transfer the data to the gateway module during predetermined Data Upload (DU) time intervals.

9. A system according to claim 8, wherein the predetermined DU time intervals are longer than the predetermined idle time duration.

10. A system according to claim 1, wherein the HCP device comprises a display device.

11. A system according to claim 10, wherein the display device is configured to display at least one of: the data or information based one the data.

12. A system according to claim 1, wherein the patient module is further configured to switch between the client mode and the AP mode, wherein the patient module is configured to prioritize communications with the HCP device over communications with the gateway module.

13. A system according to claim 1, wherein the patient module is further configured to switch between the client mode and the AP mode, wherein the patient module is configured to prioritize maintaining a connection with the gateway module over communications with the HCP device.

14. A system according to claim 1, wherein the HCP device is further configured to communicate with the cloud server and download the data previously uploaded by the gateway module.

15. A system according to claim 14, wherein, while said HCP device is downloading the data from the cloud server: the patient module is configured to transfer the data to the gateway module continuously without buffering, and the gateway module is configured to upload the data to the cloud sever continuously without buffering.

16. A system according to claim 1, wherein the patient module authorizes direct access to the data in the patient module by the HCP device by verifying that the HCP device is authorized to access the data in the patient module.

17. A system comprising:

a capsule endoscope in-vivo device; and an adhesive patch wearable device comprising communication components, the adhesive patch wearable device configured to:

receive data from the capsule endoscope in-vivo device, operate in a client mode, in which the adhesive patch wearable device transfers the data to a mobile device, and upon request from a healthcare professional (HCP) device, dynamically switch from the client mode to an access point (AP) mode, in which the adhesive patch wearable device authorizes direct access to the data in the adhesive patch wearable device by the HCP device via a direct connection between the adhesive patch wearable device and the HCP device, the direct connection having no intermediate device, wherein the mobile device is configured to receive the data from the adhesive patch wearable device while the wearable device operates in the client mode and to upload the data to a cloud server, and wherein the HCP device is configured to operate as a client to directly connect with the adhesive patch wearable device while the adhesive patch wearable device operates in the AP mode and to access the data in the adhesive patch wearable device via the direct connection between the adhesive patch wearable device and the HCP device, wherein the mobile device provides an access point while the adhesive patch wearable device operates in the client mode, wherein the access point of the mobile device is configured to terminate after an idle period of a predetermined idle time duration, wherein the adhesive patch wearable device is further configured to send, during the idle period, a pinging signal to the mobile device, the pinging signal sent at a time interval shorter than the predetermined idle time duration and operating to prevent the access point of the mobile device from terminating, and wherein in the AP mode, the adhesive patch wearable device is further configured to, periodically:

switch from the AP mode to the client mode, send the pinging signal to the mobile device, and revert to operating in the AP mode.

* * * * *